(12) United States Patent
Hagiya

(10) Patent No.: US 8,039,680 B2
(45) Date of Patent: Oct. 18, 2011

(54) PROCESS FOR PRODUCING 4-METHYL-2,3,5,6-TETRAFLUOROBENZYL ALCOHOL

(75) Inventor: Koji Hagiya, Ibaraki (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 12/525,913

(22) PCT Filed: Feb. 14, 2009

(86) PCT No.: PCT/JP2008/052914
§ 371 (c)(1),
(2), (4) Date: Aug. 5, 2009

(87) PCT Pub. No.: WO2008/099966
PCT Pub. Date: Aug. 21, 2008

(65) Prior Publication Data
US 2010/0324344 A1 Dec. 23, 2010

(30) Foreign Application Priority Data

Feb. 16, 2007 (JP) .................... 2007-035910

(51) Int. Cl.
*C07C 33/46* (2006.01)
(52) U.S. Cl. ...................................... 568/812
(58) Field of Classification Search .................. 568/812, 568/814
See application file for complete search history.

(56) References Cited

U.S. PATENT DOCUMENTS

| | | | |
|---|---|---|---|
| 4,642,398 A | 2/1987 | Cantrell | |
| 6,828,467 B2 * | 12/2004 | Miura et al. | 568/812 |
| 6,894,195 B2 * | 5/2005 | Jones et al. | 568/812 |
| 2005/0054886 A1 * | 3/2005 | Jones | 568/812 |
| 2007/0055075 A1 * | 3/2007 | Wang et al. | 560/65 |
| 2009/0099387 A1 | 4/2009 | Hagiya et al. | |

FOREIGN PATENT DOCUMENTS

| | | |
|---|---|---|
| CN | 1204104 C | 6/2005 |
| JP | 63502181 A | 8/1988 |
| JP | 2004-512319 A | 4/2004 |
| WO | 2005035474 A1 | 4/2005 |
| WO | 2007126142 A1 | 11/2007 |

OTHER PUBLICATIONS

Database CAPLUS on STN, Acc. No. 2005:295947, Feng et al., CN 1458137 (Nov. 26, 2003) (abstract).*
McMurry Yuki Kagaku (Chu), fourth edition, Kabushiki Kaisha Tokyo Kagaku Dojin Hakko, 1998 Nen, pp. 641-643, Translated by Ito et al., Chapter 17.6 "Alcohols from Reduction of Carbonyl Compounds".
Smyth, Timothy P., et al.: Inexpensive, Active KF for Nucleophilic Aromatic Displacement Reactions, Tetrahedron, 1995, vol. 51, No. 22, pp. 6363-6376.

* cited by examiner

*Primary Examiner* — Brian J Davis
(74) *Attorney, Agent, or Firm* — Panitch Schwarze Belisario & Nadell LLP

(57) ABSTRACT

A process for producing 4-methyl-2,3,5,6-tetrafluorobenzyl alcohol including the following steps: (A): a step for fluorinating 2,3,5,6-tetrachloroterephthaloyl dichloride, (B): a step for reducing the product obtained in step (A), (C): a step for chlorinating the product obtained in step (B), and Step (D): a step for hydrogenating the product obtained in step (C).

17 Claims, No Drawings

PROCESS FOR PRODUCING 4-METHYL-2,3,5,6-TETRAFLUOROBENZYL ALCOHOL

CROSS-REFERENCE TO RELATED APPLICATION

This application is a Section 371 of International Application No. PCT/JP2008/052914, filed Feb. 14, 2007, which was published in the Japanese language on Aug. 21, 2008 under International Publication No. WO 2008/099966 A1, and the disclosure of which is incorporated herein by reference.

TECHNICAL FIELD

The present invention relates to a process for producing 4-methyl-2,3,5,6-tetrafluorobenzyl alcohol.

BACKGROUND ART

It is described in US 2005/0054886 A that 4-methyl-2,3,5,6-tetrafluorobenzyl alcohol is useful as a synthetic intermediate of pesticides, and as the process for producing it, a process comprising five steps of fluorination, hydrogenation, diazotization followed by decomposition, halogenation and hydrogenation, using 2,3,5,6-tetrachloroterephthalonitrile as a starting material is described therein.

Alternatively, in CN 1458137 A, a process for producing 4-methyl-2,3,5,6-tetrafluorobenzyl alcohol comprising five steps of fluorination, esterification, reduction, bromination and hydrogenation, using 2,3,5,6-tetrachloroterephthaloyl dichloride as a starting material is described.

DISCLOSURE OF THE INVENTION

The present invention provides

<1> A process for producing 4-methyl-2,3,5,6-tetrafluorobenzyl alcohol comprising the following steps (A) to (D):
Step (A): a step for fluorinating 2,3,5,6-tetrachloroterephthaloyl dichloride,
Step (B): a step for reducing the product obtained in step (A),
Step (C): a step for chlorinating the product obtained in step (B),
Step (D): a step for hydrogenating the product obtained in step (C);
<2> The process according to <1>, wherein the fluorination is conducted using an alkali metal fluoride in step (A);
<3> The process according to <2>, wherein the alkali metal fluoride is potassium fluoride;
<4> The process according to <3>, wherein potassium fluoride is a potassium fluoride composition obtained by mixing a mixture containing potassium fluoride and 5 to 50 parts by weight of methanol per 1 part by weight of potassium fluoride with an aprotic organic solvent having a boiling point higher than that of methanol followed by removing methanol by distillation from the obtained mixture;
<5> The process according to any of <2> to <4>, wherein the fluorination is conducted in the presence of dimethyl sulfone in step (A);
<6> The process according to any of <1> to <5>, wherein the product obtained in step (A) is tetrafluoroterephthaloyl difluoride;
<7> The process according to any of <1> to <5>, wherein step (A) further contains an operation for mixing the reaction mixture obtained by fluorination with water;
<8> The process according to <7>, wherein the product obtained in step (A) is 2,3,5,6-tetrafluoroterephthalic acid;
<9> The process according to any of <1> to <5>, wherein step (A) further contains an operation for mixing the reaction mixture obtained by fluorination with a C1-C6 alcohol compound;
<10> The process according to <9>, wherein the product obtained in step (A) is 2,3,5,6-tetrafluoroterephthalic acid diester;
<11> The process according to any of <1> to <10>, wherein the reduction is conducted using at least one selected from the group consisting of a borohydride compound, an aluminum hydride compound and a silicon hydride compound in step (B);
<12> The process according to any of <1> to <10>, wherein the reduction is conducted using an alkali metal borohydride in step (B);
<13> The process according to <12>, wherein the alkali metal borohydride is sodium borohydride;
<14> The process according to <12> or <13>, wherein the reduction is conducted in the presence of at least one selected from the group consisting of an acid, water and a C1-C10 alcohol compound in step (B);
<15> The process according to any of <1> to <14>, wherein the product obtained in step (B) is 2,3,5,6-tetrafluoro-1,4-benzenedimethanol;
<16> The process according to any of <1> to <15>, wherein the chlorination is conducted using hydrogen chloride in step (C);
<17> The process according to <16>, wherein the chlorination is conducted in a two-layer system in step (C);
<18> The process according to any of <1> to <17>, wherein the product obtained in step (C) is 4-chloromethyl-2,3,5,6-tetrafluorobenzyl alcohol;
<19> The process according to any of <1> to <18>, wherein the hydrogenation is conducted using hydrogen in the presence of a metal catalyst in step (D);
<20> The process according to <19>, wherein the hydrogenation is conducted in the presence of a base in step (D).

BEST MODE FOR CARRYING OUT THE PRESENT INVENTION

First, step (A) will be illustrated. Step (A) is a step for fluorinating 2,3,5,6-tetrachloroterephthaloyl dichloride.

2,3,5,6-Tetrachloroterephthaloyl dichloride can be produced according to known methods described in JP 2-11571 B or the like.

The fluorination is usually conducted by mixing 2,3,5,6-tetrachloroterephthaloyl dichloride with a fluorinating agent.

Examples of the fluorinating agent include an alkali metal fluoride such as potassium fluoride, sodium fluoride and cesium fluoride, and hydrogen fluoride. The alkali metal fluoride is preferable and potassium fluoride is more preferable. As the fluorinating agent, commercially available one may be used and one produced according to any known methods may be used. As the fluorinating agent, one having a small particle size is preferable. Alternatively, an alkali metal fluoride in which water content is small is preferable.

As the especially preferable fluorinating agent, an alkali metal fluoride obtained by a spray-dry method is preferable. Alternatively, as the fluorinating agent, a potassium fluoride composition obtained by the following (Method 1) is also preferably used.

(Method 1): a process comprising mixing a mixture containing potassium fluoride and 5 to 50 parts by weight of methanol per 1 part by weight of potassium fluoride (hereinafter, simply referred to as the potassium fluoride mixture) with an aprotic organic solvent having a boiling point higher than that of methanol followed by removing methanol by distillation from the obtained mixture to obtain a potassium fluoride composition.

A process for preparing a potassium fluoride composition according to (Method 1) will be illustrated below.

As potassium fluoride used in (Method 1), commercially available one is usually used. Anhydrous potassium fluoride may be used, and potassium fluoride hydrate may be used. Potassium fluoride containing about 5% by weight or less of water can be also used. The particle size thereof is not particularly limited, and it may be one having a relatively large particle size (e.g. crystal) and one having a small particle size (e.g. powder).

As methanol used in (Method 1), commercially available one is usually used. It may be anhydrous methanol, and one containing about 5% by weight or less of water can be also used. The used amount of methanol is 5 to 50 parts by weight per 1 part of potassium fluoride. Examples of the obtained potassium fluoride mixture include a dispersion wherein potassium fluoride is dispersed in methanol and a solution wherein all amount of potassium fluoride are dissolved in methanol, and a solution wherein all amount of potassium fluoride are dissolved in methanol is preferable. The amount of methanol used for preparing said solution is preferably 8 parts by weight or more per 1 part by weight of potassium fluoride depending on the preparing temperature, an amount of water in methanol or the like.

The potassium fluoride mixture can be prepared by mixing potassium fluoride with methanol.

Alternatively, the potassium fluoride composition can be also prepared by a method comprising mixing potassium hydroxide with hydrogen fluoride in methanol. From the economic viewpoint, a method comprising mixing potassium hydroxide with hydrogen fluoride in methanol is preferable.

As potassium hydroxide, commercially available one is usually used as it is or if necessary, after drying. Its shape is not particularly limited, and one having any shape such as flake, rod and tablet may be used. Alternatively, it may be an aqueous solution or a solution in alcohol. An amount of water therein is preferably small. As the solution in alcohol, a solution in methanol is preferable.

As hydrogen fluoride, commercially available one is usually used as it is or after mixing with methanol or water. Hydrogen fluoride gas may be used and hydrofluoric acid may be used. From the viewpoint of operability and availability, hydrofluoric acid is preferable. When hydrogen fluoride gas is used, it may be mixed with an inert gas on the reaction to be used. When hydrofluoric acid is used, one having a high concentration is preferable. The used amount of hydrogen fluoride is usually 0.9 to 1.1 moles and preferably 0.99 to 1.01 moles per 1 mole of potassium hydroxide.

While the mixing order of potassium hydroxide, hydrogen fluoride and methanol is not particularly limited, hydrogen fluoride is preferably added to a mixture of potassium hydroxide and methanol.

The potassium fluoride composition is usually prepared under normal pressure, and may be prepared under reduced pressure or under pressure. The preparing temperature is usually 0 to 100° C. and preferably 20 to 70° C.

While the aprotic organic solvent having a boiling point higher than that of methanol may be an aprotic polar solvent and an aprotic nonpolar solvent, an aprotic polar solvent is preferable from the viewpoint of activity of the obtained potassium fluoride composition in the fluorination reaction. Examples of the aprotic polar solvent include C6-C8 aliphatic hydrocarbon solvents such as hexane, heptane, octane and cyclohexane, and aromatic hydrocarbon solvents such as benzene, toluene and xylene. Examples of the aprotic polar solvent include ether solvents such as diisopropyl ether, dibutyl ether, dioxane, diethylene glycol dimethyl ether and triethylene glycol dimethyl ether, sulfone solvents such as sulfolane, dimethylsulfone and methyl ethyl sulfone, sulfoxide solvents such as dimethylsulfoxide, diethylsulfoxide and tetramethylenesulfoxide, alkylamide solvents such as N,N-dimethylformamide, N,N-dimethylacetamide and N-methylpyrrolidone, and nitrile solvents such as butyronitrile and adiponitrile. Sulfone solvents, sulfoxide solvents and alkylamide solvents are preferable.

The used amount of the aprotic organic solvent having a boiling point higher than that of methanol may be usually 1 part by weight or more per 1 part by weight of potassium fluoride. While there is no upper limit particularly, because the productivity goes down when the amount thereof is too much, it is usually 20 parts by weight or less.

Specific examples of the method of mixing the potassium fluoride mixture with an aprotic organic solvent having a boiling point higher than that of methanol followed by removing methanol by distillation from the obtained mixture include the following methods (i) and (ii), and method (ii) is preferable in viewpoint of the activity of the obtained potassium fluoride composition.

(i) method of mixing the potassium fluoride mixture with an aprotic organic solvent having a boiling point higher than that of methanol followed by concentrating the obtained mixture to remove methanol by distillation.

(ii) method of removing methanol by distillation by adding the potassium fluoride mixture to an aprotic organic solvent under the condition at which temperature is the boiling point of methanol or more at the operating pressure.

The obtained potassium fluoride composition does not preferably essentially contain methanol from the viewpoint of the activity. From the viewpoint of easily preparation of potassium fluoride composition which does not essentially contain methanol, methanol is preferably removed by distillation using a solvent forming an azeotrope with methanol. Examples of the solvent forming an azeotrope with methanol include aromatic hydrocarbon solvents such as benzene, toluene and xylene, and aliphatic hydrocarbon solvents such as hexane and cyclohexane. When a solvent forming an azeotrope with methanol is used, said solvent is also preferably removed by distillation so that the obtained potassium fluoride composition does not essentially contain said solvent. In order to obtain a potassium fluoride composition which does not essentially contain methanol, a part of the aprotic organic solvent may be removed by distillation together with methanol and the solvent forming an azeotrope with methanol.

The operation pressure on removing methanol by distillation is usually 0.7 to 200 kPa and the operation temperature is usually 20 to 200° C.

Methanol removed by distillation may be used again for preparing the potassium fluoride mixture.

The potassium fluoride dispersion thus obtained is a mixture wherein the fine powder of potassium fluoride is dispersed in the aprotic polar organic solvent, and consists essentially of the fine powder of potassium fluoride and the above-mentioned aprotic organic solvent. The content of potassium fluoride is usually 5 to 70% by weight.

The amount of the fluorinating agent used in step (A) is usually 6 moles or more per 1 mole of tetrachloroterephthaloyl dichloride, and while there is no specific upper limit, it is preferably 6 to 10 moles from the economical viewpoint.

The fluorination of tetrachloroterephthaloyl dichloride is usually conducted in the presence of a solvent. An aprotic polar solvent is preferable as the solvent. Examples of the aprotic polar solvent include the same as used for the above-mentioned preparation of the potassium fluoride composition, and the sulfone solvent, the sulfoxide solvent or the alkylamide solvent is more preferable, the sulfone solvent is furthermore preferable and dimethyl sulfone is especially preferable.

While the used amount of the solvent is not particularly limited, and it is usually 0.1 to 20 parts by weight per 1 part by weight of tetrachloroterephthaloyl dichloride.

The reaction temperature is usually in a range of 120 to 200° C.

When dimethyl sulfone is used as the solvent, the reaction is preferably conducted further in the presence of an inert organic solvent on the reaction. As the inert organic solvent on the reaction, an inert organic solvent on the reaction having a lower boiling point than that of dimethyl sulfone and having a lower melting point than that of dimethyl sulfone is preferable, and an inert organic solvent on the reaction having a boiling point of 100 to 200° C. and having a lower melting point than that of dimethyl sulfone is more preferable, and an inert organic solvent on the reaction having a boiling point of 100 to 200° C. and having a melting point of 50° C. or less is especially preferable.

Examples of the inert organic solvent on the reaction include ether solvents such as dioxane and diethylene glycol dimethyl ether, N,N-dialkylamide solvents such as N,N-dimethylacetamide, aromatic hydrocarbon solvents such as toluene, xylene, chlorobenzene and benzonitrile, and aliphatic hydrocarbon solvents such as octane and decane. The used amount thereof is usually 0.5 part by weight or less and preferably 0.2 part by weight or less per 1 part by weight of dimethyl sulfone.

The fluorination of tetrachloroterephthaloyl dichloride is conducted by mixing tetrachloroterephthaloyl dichloride and the fluorinating agent, as necessary, in the presence of the solvent, followed by conducting stirring at a predetermined temperature, and the mixing order is not particularly limited. When the alkali metal fluoride is used as the fluorinating agent, the fluorination is preferably conducted after removing water contained in the alkali metal fluoride. Examples of the method for removing water containing in the alkali metal fluoride include a method comprising mixing the alkali metal fluoride with the solvent followed by heating under reduced pressure, and a method comprising heating a mixture of an organic solvent forming an azeotrope with water, the alkali metal fluoride and the solvent to conduct an azeotropic dehydration.

The fluorination is usually conducted at normal pressure and may be conducted under pressure. The progress of the reaction can be checked by a conventional analytical means such as gas chromatography and liquid chromatography.

The reaction mixture after fluorination usually contains tetrafluoroterephthaloyl difluoride as a product, and the reaction mixture containing tetrafluoroterephthaloyl difluoride may be used as it is for next step (B), and tetrafluoroterephthaloyl difluoride may be isolated by concentrating the reaction mixture to use for step (B).

Alternatively, the obtained reaction mixture is mixed with water or a C1-C6 alcohol compound and then the obtained product may be used for step (B).

When the reaction mixture is mixed with water, 2,3,5,6-tetrafluoroterephthalic acid is obtained as the product, and when the reaction mixture is mixed with the C1-C6 alcohol compound, a 2,3,5,6-tetrafluoroterephthalic acid diester is obtained as the product.

Examples of the C1-C6 alcohol compound include a linear, branched chain or cyclic alcohol compound such as methanol, ethanol, n-propanol, isopropanol, n-butanol, tert-butanol and cyclohexanol. As these, a commercially available one is usually used.

While the used amount of the C1-C6 alcohol compound is not particularly limited, it is usually 2 to 50 moles per 1 mole of tetrafluoroterephthaloyl difluoride contained in the reaction mixture.

The mixing of the reaction mixture with water or the C1-C6 alcohol compound may be carried out in the presence of a water-immiscible organic solvent. Examples of the water-immiscible organic solvent include aromatic hydrocarbon solvents such as toluene, xylene and chlorobenzene, aliphatic hydrocarbon solvents such as pentane, hexane and heptane, halogenated aliphatic hydrocarbon solvents such as dichloromethane, dichloroethane and chloroform, ether solvents such as diethyl ether and methyl tert-butyl ether, and ester solvents such as ethyl acetate. The used amount thereof is not particularly limited.

When the reaction mixture is mixed with water or the C1-C6 alcohol compound, hydrogen fluoride is usually generated. Therefore, the mixing is preferably conducted while removing hydrogen fluoride such as mixing in the presence of a base, mixing while blowing an inert gas therein and mixing under reduced pressure.

Examples of the base include tertiary amine such as triethylamine and diisopropylethylamine, nitrogen-containing aromatic compounds such as pyridine, collidine and quinoline, alkali metal carboxylates such as sodium acetate, alkali metal alcoholates such as sodium methylate and sodium ethylate, alkali metal hydroxides such as sodium hydroxide and potassium hydroxide, alkaline earth metal hydroxides such as calcium hydroxide and magnesium hydroxide, alkali metal carbonates such as sodium carbonate and potassium carbonate, alkali metal hydrogen carbonates such as sodium hydrogen carbonate and potassium hydrogen carbonate, alkaline earth metal carbonates such as calcium carbonate and magnesium carbonate, and alkaline earth metal hydrogen carbonates such as calcium hydrogen carbonate and magnesium hydrogen carbonate. Nitrogen-containing aromatic compounds, alkali metal carbonates, alkali metal hydrogen carbonates, alkaline earth metal carbonates or alkaline earth metal hydrogen carbonates is preferable, and alkali metal carbonates, alkali metal hydrogen carbonates, alkaline earth metal carbonates or alkaline earth metal hydrogen carbonates is more preferable.

The used amount of the base may be amount enough to neutralize the generated hydrogen fluoride, and it is usually 2 to 5 moles per 1 mole of tetrafluoroterephthaloyl difluoride.

Examples of the inert gas include nitrogen, carbon dioxide and air.

When the mixing is conducted under reduced pressure, pressure is usually 6 to 100 kPa.

The mixing order of the reaction mixture with water or the C1-C6 alcohol compound is not particularly limited. When the mixing is carried out in the presence of the base, water or the C1-C6 alcohol compound is preferably added to a mixture of the reaction mixture and the base, or the base and water or the C1-C6 alcohol compound are preferably added to the reaction mixture.

The mixing temperature is not particularly limited, and it is usually 0 to 100° C. When the mixing is carried out in the presence of the base, it is preferably 0 to 30° C.

The reaction mixture obtained after completion of the mixing contains tetrafluoroterephthalic acid or a tetrafluoroterephthalic acid diester as a product, and while this may be used as it is for next step (B), an organic layer containing the product, which is obtained by conducting conventional post-treatment such as separation and filtration, is usually used for step (B). Alternatively, the product may be isolated from the organic layer by isolation means such as concentration and crystallization to use for step (B).

Examples of the tetrafluoroterephthalic acid diester include dimethyl 2,3,5,6-tetrafluoroterephthalate, diethyl 2,3,5,6-tetrafluoroterephthalate, di(n-propyl) 2,3,5,6-tetrafluoroterephthalate, diisopropyl 2,3,5,6-tetrafluoroterephthalate, di(n-butyl) 2,3,5,6-tetrafluoroterephthalate and di(tert-butyl) 2,3,5,6-tetrafluoroterephthalate.

Next, step (B) will be illustrated. Step (B) is a step for reducing the product obtained in step (A).

The reduction of the product obtained in step (A) is usually conducted by contacting the product obtained in step (A) with a reducing agent.

As the reducing agent, at least one selected from the group consisting of a borohydride compound, an aluminum hydride compound and a silicon hydride compound. Examples of the borohydride compound include an alkali metal borohydride such as sodium borohydride, lithium borohydride and potassium borohydride, an alkaline earth metal borohydride such as calcium borohydride and magnesium borohydride, and a borane compound such as diborane and borane-tetrahydrofuran complex. Examples of the aluminum hydride compound include an aluminum metal hydride such as lithium aluminum hydride, and a dialkylaluminum hydride such as diisobutylaluminum hydride. Examples of the silicon hydride compound include alkylsilyl hydrides such as triethylsilyl hydride, triisopropylsilyl hydride, diethylsilyl hydride and 1,1,2,2-tetramethyldisilane; and silanes such as monosilane and disilane. Among them, a borohydride compound is preferable and an alkali metal borohydride is more preferable and sodium borohydride is furthermore preferable.

A commercially available reducing agent may be used and one prepared according to known methods may be used. The reducing agent previously prepared may be used and it may be prepared in the reaction system.

The used amount of the reducing agent is usually 1 to 5 moles and preferably 2 to 3 moles per 1 mole of the product obtained in step (A).

The reduction is usually conducted in a solvent. Examples of the solvent include ether solvents such as diethyl ether, methyl tert-butyl ether, tetrahydrofuran, dioxane and diisopropyl ether, and aromatic hydrocarbon solvents such as toluene, xylene and chlorobenzene. While the used amount thereof is not particularly limited, it is practically 100 parts by weight or less per 1 part by weight of the product obtained in step (A) considering volume efficiency.

When an alkali metal borohydride is used as the reducing agent, the reduction is preferably conducted in the presence of at least one selected from the group consisting of an acid, water and a C1-C10 alcohol compound in order to proceed the reduction in a good yield.

Examples of the acid include mineral acids, carboxylic acids and sulfonic acids, and mineral acids are preferable. Examples of the mineral acid include hydrochloric acid, sulfuric acid and phosphoric acid, and hydrochloric acid and sulfuric acid are preferable. Examples of the carboxylic acid include aliphatic carboxylic acids such as formic acid, acetic acid, trifluoroacetic acid, propionic acid, butanoic acid and oxalic acid, and aromatic carboxylic acids such as benzoic acid. Examples of the sulfonic acid include aliphatic sulfonic acids such as methanesulfonic acid, ethanesulfonic acid and trifluoromethanesulfonic acid, and aromatic sulfonic acids such as benzenesulfonic acid and p-toluenesulfonic acid. As the acid, commercially available one is usually used. The acid may be used as it is, and it may be mixed with water or the above-mentioned solvent to use. When the acid is used as an aqueous solution, the concentration of acid is usually 5% by weight or more, and one having a high concentration thereof is preferable. The used amount of the acid is usually 0.2 to 5 moles and preferably 0.2 to 2 moles per 1 mole of the alkali metal borohydride based on protons.

The used amount of water is usually 0.5 to 10 moles and preferably 0.9 to 4 moles per 1 mole of the alkali metal borohydride.

Examples of the C1-C10 alcohol compound include aliphatic alcohols such as methanol, ethanol, n-propanol, isopropanol, n-butanol and tert-butanol, and aromatic alcohols such as phenol and benzyl alcohol, and aliphatic alcohols are preferable and methanol is more preferable. The used amount thereof is not particularly limited, and while the excess amount thereof may be used also to serve as the solvent, it is usually is 0.2 to 50 moles per 1 mole of the alkali metal borohydride.

The reduction is usually conducted by contacting the product obtained in step (A) with the reducing agent in a solvent. When an alkali metal borohydride is used as the reducing agent, it is preferred that a mixture of the product obtained in step (A), the alkali metal borohydride and the solvent is stirred at a predetermined reaction temperature and that at least one selected from the group consisting of an acid, water and a C1-C10 alcohol compound is added thereto.

The reduction temperature is usually 0 to 150° C. The reduction temperature when the reduction is conducted using an alkali metal borohydride as the reducing agent in the presence of an acid or a C1-C10 alcohol compound is preferably 20 to 80° C. The reduction temperature when the reduction is conducted using an alkali metal borohydride as the reducing agent in the presence of water is preferably 40 to 80° C.

While the reduction is usually carried out at normal pressure, it may be carried out under pressure. The progress of the reduction can be checked by a conventional analytical means such as gas chromatography and liquid chromatography.

After completion of the reduction, the reaction mixture containing 2,3,5,6-tetrafluoro-1,4-benzenedimethanol as the product is obtained. While the obtained reaction mixture may be used as it is for next step (C), an aqueous mineral acid solution such as hydrochloric acid, sulfuric acid, phosphoric acid and nitric acid is usually mixed with the obtained reaction mixture and as necessary, a treatment such as neutralization and extraction is conducted, to obtain an organic layer containing 2,3,5,6-tetrafluoro-1,4-benzenedimethanol, and the organic layer is used for step (C). Alternatively, the product may be isolated by concentrating the organic layer to use for step (C).

Next, step (C) will be illustrated. Step (C) is a step for chlorinating the product obtained in step (B).

The chlorination is usually conducted by contacting the product obtained in step (B) with a chlorinating agent.

The chlorinating agent may be one used for chlorination of an alcoholic hydroxyl group, and examples thereof include hydrogen chloride, thionyl chloride, phosphorous trichloride and phosphorous oxychloride, and hydrogen chloride is preferable. As these chlorinating agents, commercially available one is usually used. As hydrogen chloride, any of hydrogen chloride gas, an organic solvent solution of hydrogen chloride and hydrochloric acid can be used, and hydrochloric acid is preferable from the viewpoint of operability and availability. Hydrogen chloride gas may be mixed with an inert gas on the reaction to use. When hydrochloric acid is used, one having a high concentration is preferable, and a commercially available concentrated hydrochloric acid is preferable. Examples of the organic solvent solution of hydrogen chloride include hydrogen chloride/dioxane solution, hydrogen chloride/tetrahydrofuran solution and hydrogen chloride/dimethoxyethane solution.

The used amount of the chlorinating agent is usually 1 to 20 moles per 1 mole of the product obtained in step (B). When hydrogen chloride is used as the chlorinating agent, the used amount thereof is preferably 5 to 15 moles per 1 mole of the product obtained in step (B).

The chlorination is usually carried out in the presence of an solvent. Examples of the solvent include aromatic hydrocarbon solvents such as toluene, xylene and chlorobenzene, aliphatic hydrocarbon solvents such as hexane, heptane and cyclohexane, ether solvents such as tetrahydrofuran and dioxane, and water. These solvents may be used alone and two or more thereof may be mixed to use. When hydrogen chloride is used as the chlorinating agent, the chlorination is preferably conducted in a two-layer system of an aqueous layer and an organic layer using a mixed solvent of water-immiscible solvent such as aromatic hydrocarbon solvents and aliphatic hydrocarbon solvents and water.

While the used amount of the solvent is not particularly limited, it is practically 100 parts by weight or less per 1 part by weight of the product obtained in step (B) considering the volume efficiency.

The chlorination temperature is usually 50 to 110° C.

The chlorination is usually carried out by mixing the product obtained in step (B) with the chlorinating agent. The mixing order is not particularly limited.

While the chlorination is usually conducted at normal pressure, it may be conducted under pressure. In order to react the chlorinating agent with the product obtained in step (B) efficiently, the chlorination may be conducted in a closed container such as autoclave.

The progress of the chlorination can be checked by a conventional analytical means such as gas chromatography and liquid chromatography.

After completion of the chlorination, the reaction mixture containing 4-chloromethyl-2,3,5,6-tetrafluorobenzenemethanol as the product is obtained. While the obtained reaction mixture may be used as it is for next step (D), it is preferable that an organic layer containing 4-chloromethyl-2,3,5,6-tetrafluorobenzenemethanol is obtained by conducting a conventional posttreatment such as separation and extraction and that the organic layer is used for step (D). As necessary, water or a water-immiscible organic solvent may be used for the posttreatment. Alternatively, 4-chloromethyl-2,3,5,6-tetrafluorobenzenemethanol may be isolated by concentrating the obtained organic layer to use for step (D).

The unreacted product obtained in step (B) is sometimes contained in the aqueous layer obtained in the above-mentioned posttreatment, the aqueous layer is neutralized with a base followed by conducting a treatment such as extraction and concentration to be able to recover unreacted product obtained in step (B). As the base, an inorganic base such as sodium hydroxide, potassium hydroxide, sodium carbonate and potassium carbonate or an aqueous solution thereof is usually used.

Last, step (D) will be illustrated. Step (D) is a step for hydrogenating the product obtained in step (C).

The hydrogenation is usually conducted by contacting the product obtained in step (C) with hydrogen in the presence of a metal catalyst. While the hydrogen pressure is not particularly limited, it is usually normal pressure to 1 MPa.

As the metal catalyst, a metal catalyst containing at least one metal atom selected from the group consisting of cobalt, iron, nickel, platinum, palladium and rhenium is used. As the metal catalyst, the above-mentioned metal or an alloy thereof may be used as it is, and they may be supported on a carrier to use.

As the metal catalyst, a sponge-metal catalyst can also be used. Herein, "sponge-metal catalyst" means a porous metal catalyst obtained by eluting a metal soluble in an alkali or an acid with an alkali or an acid from an alloy of a metal insoluble in an alkali or an acid such as nickel and cobalt and a metal soluble in an alkali or an acid such as aluminum, silicon, zinc and magnesium. Examples thereof include sponge-cobalt and sponge-nickel.

When the metal or the alloy is used as it is as the metal catalyst, the metal or the alloy having a small particle size is preferably used. Alternatively, when the metal catalyst supported on the carrier is used, examples of the carrier include active carbon, alumina, silica and zeolite, and active carbon is preferable from the viewpoint of availability, and a carrier having a small particle size is preferable from the viewpoint of reaction activity.

A metal catalyst containing water may be used.

As the metal catalyst, one wherein palladium metal is supported on the carrier is preferable, and palladium/carbon is more preferable.

The used amount of the metal catalyst depends on its form, and it is usually 0.1 to 150% by weight per 1 part of the product obtained in step (C).

The hydrogenation is usually conducted in the presence of a solvent. The solvent is not particularly limited in so far as it is an inert one on the reaction, and examples thereof include aromatic hydrocarbon solvents such as toluene, xylene and chlorobenzene, aliphatic hydrocarbon solvents such as pentane, hexane and heptane, ether solvents such as diethyl ether and methyl tert-butyl ether, ester solvents such as ethyl acetate, alcohol solvents such as methanol, ethanol, isopropanol, n-butanol and tert-butanol and water. These solvents may be used alone and may be mixed to use.

While the used amount of the solvent is not particularly limited, it is practically 20 parts by weight or less per 1 part by weight of the product obtained in step (C) considering volume efficiency.

The hydrogenation temperature is usually 50 to 150° C.

Because hydrogen chloride is generated along with the progression of the hydrogenation, the hydrogenation is preferably carried out in the presence of a base. Examples of the base include inorganic bases such as alkali metal hydroxides such as sodium hydroxide and potassium hydroxide, alkaline earth metal hydroxides such as magnesium hydroxide and calcium hydroxide, alkali metal carbonates such as sodium carbonate and potassium carbonate, alkaline earth metal carbonates such as magnesium carbonate and calcium carbonate, and alkaline earth metal oxides such as magnesium oxide and calcium oxide. Alkaline earth metal oxides are preferable and magnesium oxide is more preferable.

The progress of the hydrogenation can be checked by a conventional analytical means such as gas chromatography and liquid chromatography.

After completion of the hydrogenation, the reaction mixture containing 4-methyl-2,3,5,6-tetrafluorobenzenemethanol as the product is obtained. 4-Methyl-2,3,5,6-tetrafluorobenzenemethanol can be isolated by removing insoluble matters such as the metal catalyst from the obtained reaction mixture by filtration, adding water and if necessary, a water-immiscible organic solvent to conduct washing and then concentrating the obtained organic layer. Examples of the water-immiscible organic solvent include aromatic hydrocarbon solvents such as toluene, xylene and chlorobenzene, aliphatic hydrocarbon solvents such as pentane, hexane and heptane, halogenated hydrocarbon solvents such as dichloromethane, dichloroethane and chloroform, ether solvents such as diethyl ether and methyl tert-butyl ether, and ester solvents such as ethyl acetate. The obtained 4-methyl-2,3,5,6-tetrafluorobenzenemethanol may be further purified by a conventional purification means such as distillation and column chromatography.

Insoluble matters such as the metal catalyst removed from the reaction mixture may be sometimes used again as a metal catalyst in the present step (D) as it is or after washing with an organic solvent, water, an acid or a base.

EXAMPLES

The present invention will be illustrated in more detail by Examples below. The present invention is not limited to these Examples.

Example 1

<Step (A)>
A solution wherein potassium fluoride is dissolved completely in methanol was prepared by mixing 30 g of potassium fluoride with 350 g of methanol followed by heating for 30 minutes under reflux. Into a 200 mL flask equipped with a reflux condenser, 110 g of sulfolane was charged followed by heating to 140° C. To this, the solution wherein potassium fluoride is dissolved completely in methanol was added dropwise and methanol was removed by distillation along with the addition dropwise. After completion of adding the solution dropwise and hardly removing methanol by distillation, methanol was further removed by distillation at 160° C. at 2.7 kPa to obtain a potassium fluoride composition which does not essentially contain methanol.

The obtained potassium fluoride composition was cooled to 100° C. and was mixed with 22 g of tetrachloroterephthaloyl dichloride. The obtained mixture was stirred for 3.5 hours at 145° C. to conduct the reaction. The obtained reaction mixture was cooled to 100° C. and then, 100 g of toluene was added thereto followed by further cooling to room temperature. To the obtained mixture, 15 g of methanol was added dropwise followed by stirring for 12 hours at room temperature while removing generated hydrogen fluoride out the flask by blowing nitrogen gas therein. The precipitated solids were removed by filtration and the solids were washed with 10 g of toluene. The obtained filtrate and wash liquid were mixed and 100 g of water was added thereto, and then, pH of the aqueous layer was adjusted to 7 with 600 mg of potassium carbonate. The obtained mixture was separated to an organic layer and an aqueous layer. The obtained organic layer was concentrated with an evaporator (reduced pressure value 10 to 100 kPa, water bath temperature 30 to 50° C.) to obtain the oily residue. The residue was mixed with 110 g of water and then the crystals were precipitated. Further, it was concentrated with an evaporator (operation pressure 10 to 100 kPa, water bath temperature 30 to 50° C.) to remove toluene contained in the residue together with about 5 g of water. After cooling to room temperature, precipitated crystals were filtrated and then dried to obtain 17.4 g of a pale yellow crystals of dimethyl 2,3,5,6-tetrafluoroterephthalate. The crystals were analyzed by gas chromatography area percentage method to find out that the purity thereof was 92%. Yield: 93%.

Example 2

<Step (A)>
To a 500 mL flask equipped with a reflux condenser, 23 g of potassium fluoride (spray-dry), 85 g of dimethyl sulfone and 30 g of toluene were charged followed by heating to 130° C. to conduct removal of water. After dehydration, the obtained mixture was maintained at 140° C. until toluene was not removed by distillation. Further, toluene was almost completely removed by distillation by reducing the pressure to 20 mmHg, and then, the pressure was brought back to normal pressure followed by cooling to 100° C. to obtain a potassium fluoride composition. To the obtained potassium fluoride composition, 17 g of tetrachloroterephthaloyl dichloride and 1.5 g of toluene were added followed by mixing at 145° C. for 3 hours to conduct the reaction. The obtained reaction mixture was cooled to 110° C. and then, 300 g of toluene was added thereto followed by further cooling to 60° C. To the obtained mixture, 100 g of methanol was added followed by stirring for 10 hours at room temperature while blowing nitrogen gas therein. The obtained mixture was concentrated, and to the obtained residue, 200 g of water and 6.9 g of potassium carbonate were added. The obtained mixture was stirred and then, separated to obtain an organic layer. The organic layer was concentrated and the obtained residue was dried to obtain 13.2 g of a pale yellow crystals of dimethyl 2,3,5,6-tetrafluoroterephthalate. The crystals were analyzed by gas chromatography internal standard method to find out that the content of dimethyl 2,3,5,6-tetrafluoroterephthalate was 90.0% by weight. Yield: 89%.

Example 3

<Step (A)>
Thirty grams of methanol and 100 g of tolune were charged into a 200 mL flask equipped with a reflux condenser and a Soxhlet extraction tube, and 20 g of potassium fluoride was charged into the Soxhlet extraction tube. The content in the flask was heated to 100° C. to reflux methanol for 18 hours. Pottasium fluoride in the Soxhlet extraction tube was completely disappeared to obtain a potassium fluoride dispersion. The potassium fluoride dispersion was heated to 90 to 100° C. at normal pressure to remove 30 g of a mixed solution of methanol and toluene by distillation. To this, 100 g of toluene was added followed by further removing 100 g of a mixed solution of methanol and toluene by distillation. The obtained mixture containing potassium fluoride was filtrated and the obtained fine powders were dried to obtain 19.7 g of fine powders of potassium fluoride.

Into a 50 mL flask equipped with a reflux condenser and a tube for separating water, 960 mg of the obtained fine powders of potassium fluoride, 3 g of sulfolane and 3 g of toluene were charged. The obtained mixture was refluxed at 130° C. for 30 minutes to remove water contained therein and toluene was further removed at 140° C. by distillation to obtain a potassium fluoride composition.

The obtained potassium fluoride composition was cooled to 100° C. and was mixed with 680 mg of tetrachloroterephthaloyl dichloride. The obtained mixture was stirred for 4 hours at 150° C. to conduct the reaction. The obtained reaction mixture was cooled to room temperature and then, 5 g of methanol was added thereto followed by stirring at room temperature for 1 hour. To this, 10 g of ethyl acetate was added to obtain a mixture containing dimethyl 2,3,5,6-tetrafluoroterephthalate. The obtained mixture was analyzed by gas chromatography internal standard method to find out that the yield thereof was 70%. Alternatively, dimethyl 2,3,5-trifluoro-6-chloroterephthalate was generated in a yield of 16% and dimethyl difluorodichloroterephthalate was generated in a yield of 11% (sum of three isomers).

Example 4

<Step (A)>

Into a 200 mL flask equipped with a reflux condenser, 500 g of sulfolane was charged followed by heating to an inner temperature of 140° C. To 1 L Erlenmeyer flask, 150 g of potassium fluoride and 500 g of methanol were added, and a methanol solution of potassium fluoride was obtained from the obtained mixture by decantation. The obtained methanol solution was added dropwise into the above-mentioned sulfolane and methanol was distilled away along with adding dropwise. The distilled methanol was corrected and mixed with solid potassium fluoride obtained by the above decantation to prepare a methanol solution of potassium fluoride. The methanol solution was added dropwise to the above-mentioned 200 mL flask and methanol was distilled away along with adding dropwise. After hardly distilling methanol away, methanol was further removed by distillation under the condition of 160° C. at 2.7 kPa to obtain a potassium fluoride composition which does not essentially contain methanol.

The obtained potassium fluoride composition was cooled to 100° C. and was mixed with 110 g of tetrachloroterephthaloyl dichloride. The obtained mixture was stirred at 145° C. for 10 hours to conduct the reaction. The obtained reaction mixture was cooled to 100° C. and then, 300 g of toluene was added thereto followed by cooling to room temperature. To the obtained mixture, 75 g of methanol was added dropwise followed by stirring for 12 hours at room temperature while removing generated hydrogen fluoride out the flask by blowing nitrogen gas therein. The precipitated solids were removed by filtration. The obtained solids were washed with 50 g of methanol. The obtained filtrate and wash liquid were mixed and 500 g of water was added thereto followed by adjusting pH of an aqueous layer to 8 with 4 g of potassium carbonate. The obtained mixture was separated to an organic layer and an aqueous layer, and the obtained organic layer was concentrated with an evaporator (reduced pressure value 10 to 100 kPa, water bath temperature 30 to 50° C.) to obtain the oily residue. The residue was mixed with 300 g of water and then the crystals were precipitated. Further, it was concentrated with an evaporator (operation pressure 10 to 100 kPa, water bath temperature 30 to 50° C.) to remove toluene contained in the residue together with about 20 g of water. After cooling to room temperature, precipitated crystals were filtrated and then dried to obtain 82.2 g of a pale yellow crystals of dimethyl 2,3,5,6-tetrafluoroterephthalate. The crystals were analyzed by gas chromatography internal standard method to find out that the purity thereof was 89%. Yield: 85%.

Example 5

<Step (A)>

Into a 200 mL flask equipped with a reflux condenser, 97 g of sulfolane was charged followed by heating to 140° C. To this, a solution wherein potassium fluoride was completely dissolved in methanol, which was prepared by mixing 30 g of potassium fluoride with 350 g of methanol followed by heating for 30 minutes under reflux, was added dropwise, and methanol was distilled away along with adding dropwise. After adding the solution dropwise was completed and methanol hardly was distilled away, 10 g of toluene was added thereto followed by further heating at 140° C. After hardly distilling toluene away, residual methanol and toluene were further removed by distillation under the condition of 160° C. at 2.7 kPa to obtain a potassium fluoride composition which does not essentially contain methanol.

The obtained potassium fluoride composition was cooled to 100° C. and was mixed with 22 g of tetrachloroterephthaloyl dichloride. The obtained mixture was stirred at 145° C. for 4 hours to conduct the reaction. The obtained reaction mixture was cooled to 100° C. and then, 100 g of toluene was added thereto followed by further cooling to room temperature. The obtained mixture was filtrated to remove insoluble matters. The obtained insoluble matters were washed with 20 g of toluene and the obtained filtrate and wash liquid were mixed. The obtained solution was added dropwise into a mixture of 7.6 g of potassium hydroxide and 100 g of water, and then, the precipitated solids were obtained by filtration. The obtained solids were washed with 10 g of water followed by drying to obtain crystals of 2,3,5,6-tetrafluoroterephthalic acid. The obtained filtrate and wash liquid were mixed and the obtained mixed liquid was separated to an organic layer and an aqueous layer. The obtained aqueous layer was concentrated until it was reduced by about half and the precipitated solids were filtrated followed by drying to obtain crystals of 2,3,5,6-tetrafluoroterephthalic acid. The obtained crystals were mixed to obtain 15.9 g of 2,3,5,6-tetrafluoroterephthalic acid. The crystals were analyzed by liquid chromatography absolute calibration curve method to find out that the purity thereof was 85%. Yield: 88%.

Example 6

<Step (A)>

Into a 500 mL flask equipped with a reflux condenser, 315 g of sulfolane was charged followed by reducing the pressure to 37.3 kPa and then heating to 130° C. To this, a solution prepared by dissolving 61.3 g of potassium fluoride in 810 g of methanol was added dropwise over 6 hours, and methanol was distilled away along with adding dropwise. After adding the solution dropwise was completed and methanol hardly was distilled away, residual methanol was removed by distillation under the condition of 160° C. at 2.7 kPa to obtain a potassium fluoride composition which does not essentially contain methanol.

The obtained potassium fluoride composition was cooled to 120° C. at normal pressure and was mixed with 45 g of tetrachloroterephthaloyl dichloride. The obtained mixture was stirred at 140° C. for 4 hours to conduct the reaction. The obtained reaction mixture was cooled to 40° C. After reducing the pressure to 2.7 kPa, it was heated to 160° C. to obtain 25.2 g of the fraction of a top temperature of 95 to 96° C. 2,3,5,6-Tetrafluoroterephthaloyl difluoride was contained in the fraction, and the content thereof was 94.6% by weight. Yield: 75%.

Example 7

<Step (B)>

Into a 200 mL flask equipped with a reflux condenser, 9.4 g of sodium borohydride and 100 g of tetrahydrofuran were charged at room temperature. To this, a solution prepared by dissolving 28.5 g of dimethyl 2,3,5,6-tetrafluoroterephthalate in 100 g of tetrahydrofuran was added. The obtained mixture was adjusted to 60° C. and then, 26 g of 35% by weight hydrochloric acid was added dropwise thereto over 5 hours while stirring. The obtained mixture was stirred for 2 hours at the same temperature, and then cooled to room temperature. To the obtained reaction mixture, 120 g of 5% by weight hydrochloric acid was added followed by stirring and leaving at rest. The upper organic layer was obtained and 100 g of toluene was added thereto followed by washing twice with 30 g of water. The obtained organic layer was concentrated to obtain 26.0 g of white crystals of 2,3,5,6-tetrafluorobenzenedimethanol. The crystals were analyzed by liquid chromatography internal standard method to find out that the purity thereof was 80%. Yield: 92%.

Example 8

<Step (B)>

Into a 200 mL flask equipped with a reflux condenser, 4.6 g of sodium borohydride and 50 g of tetrahydrofuran were charged at room temperature. To this, a solution prepared by dissolving 14.7 g of dimethyl 2,3,5,6-tetrafluoroterephthalate in 50 g of tetrahydrofuran was added. The obtained mixture was adjusted to 60° C. and then, 13 g of 45% by weight sulfuric acid was added dropwise thereto over 5 hours while stirring. The obtained mixture was stirred for 2 hours at the same temperature, and then, cooled to room temperature. To the obtained reaction mixture, 50 g of water was added followed by stirring and leaving at rest. The upper organic layer was obtained and 50 g of toluene was added thereto followed by washing twice with 30 g of water. The obtained organic layer was concentrated to obtain 12.4 g of white crystals of 2,3,5,6-tetrafluorobenzenedimethanol. The crystals were analyzed by liquid chromatography internal standard method to find out that the purity thereof was 85.7%. Yield: 92%.

Example 9

<Step (B)>

Into a 200 mL flask equipped with a reflux condenser, 1.6 g of sodium borohydride and 30 g of tetrahydrofuran were charged at room temperature. To this, a solution prepared by dissolving 5.1 g of dimethyl 2,3,5,6-tetrafluoroterephthalate in 20 g of tetrahydrofuran was added. To the obtained mixture, a solution obtained by mixing 4.4 g of 35% by weight hydrochloric acid with 6 g of tetrahydrofuran was added dropwise over 5 hours while stirring at room temperature. The obtained mixture was stirred for 2 hours at 25 to 30° C. To the obtained reaction mixture, 30 g of 5% by weight hydrochloric acid was added followed by stirring and leaving at rest. The upper organic layer was obtained and 50 g of toluene was added thereto followed by washing twice with 20 g of water. The obtained organic layer was concentrated to obtain 4.4 g of white crystals of 2,3,5,6-tetrafluorobenzenedimethanol. The crystals were analyzed by liquid chromatography internal standard method to find out that the purity thereof was 85.4%. Yield: 93%.

Example 10

<Step (B)>

Into a 200 mL flask equipped with a reflux condenser, 1.7 g of sodium borohydride and 30 g of tetrahydrofuran were charged at room temperature. To this, a solution prepared by dissolving 6.0 g of dimethyl 2,3,5,6-tetrafluoroterephthalate, which was obtained in Example 4, in 20 g of tetrahydrofuran was added. The obtained mixture was adjusted to 50° C. and then, a solution obtained by mixing 10.2 g of 35% by weight hydrochloric acid with 10 g of tetrahydrofuran was added dropwise thereto over 5 hours while stirring. The obtained mixture was stirred for 2 hours at the same temperature followed by cooling to room temperature. To the obtained reaction mixture, 30 g of 5% by weight hydrochloric acid was added followed by stirring and leaving at rest. The upper organic layer was obtained and 50 g of toluene was added thereto followed by washing twice with 30 g of water. The obtained organic layer was concentrated to obtain 4.3 g of white crystals of 2,3,5,6-tetrafluorobenzenedimethanol. The crystals were analyzed by liquid chromatography internal standard method to find out that the purity thereof was 89%. Yield: 91%.

Example 11

<Step (B)>

Into a 200 mL flask equipped with a reflux condenser, 1.7 g of sodium borohydride and 30 g of tetrahydrofuran were charged at room temperature. To this, a solution prepared by dissolving 6.0 g of dimethyl 2,3,5,6-tetrafluoroterephthalate, which was obtained in Example 4, in 20 g of tetrahydrofuran was added. The obtained mixture was adjusted to 50° C. and then, a solution obtained by mixing 3 g of acetic acid with 10 g of tetrahydrofuran was added dropwise over 5 hours while stirring. The obtained mixture was stirred for 2 hours at the same temperature followed by cooling to room temperature. To the obtained reaction mixture, 30 g of 5% by weight hydrochloric acid was added followed by stirring and leaving at rest. The upper organic layer was obtained and 50 g of toluene was added thereto followed by washing twice with 30 g of water. The obtained organic layer was concentrated to obtain 4.1 g of white crystals of 2,3,5,6-tetrafluorobenzenedimethanol. The crystals were analyzed by liquid chromatography internal standard method to find out that the purity thereof was 94%. Yield: 92%.

Example 12

<Step (B)>

Into a 200 mL flask equipped with a reflux condenser, 2.61 g of sodium borohydride, 26.8 g of tetrahydrofuran and 8.94 g of dimethyl 2,3,5,6-tetrafluoroterephthalate were charged. The obtained mixture was adjusted to 55° C. and then, 26.7 g of methanol was added dropwise thereto over 80 minutes while stirring. The obtained mixture was stirred for 6.5 hours at the same temperature followed by cooling to room temperature and then further stirring for 20 hours. To the obtained reaction mixture, 24.5 g of 10% by weight hydrochloric acid was added dropwise over 1 hour at 25 to 30° C. followed by stirring for 1 hour at the same temperature. Further, 8 g of 23% by weight aqueous sodium hydroxide solution was added thereto to stir. The obtained solution was concentrated. To the concentrated residue, 100 g of water was added and the obtained mixture was extracted three times with 70 g of ethyl acetate. The obtained organic layers were mixed and dried over anhydrous magnesium sulfate. After removing magnesium sulfate by filtration, the obtained filtrate was concentrated to obtain 6.38 g of white crystals of 2,3,5,6-tetrafluorobenzenedimethanol. The crystals were analyzed by gas chromatography internal standard method to find out that the content thereof was 92.5%. Yield: 84%.

Example 13

<Step (B)>

Into a 200 mL flask equipped with a reflux condenser, 1.66 g of sodium borohydride, 20.0 g of methyl tert-butyl ether and 5.32 g of dimethyl 2,3,5,6-tetrafluoroterephthalate were charged. The obtained mixture was adjusted to 55° C. and then, 18.0 g of methanol was added dropwise thereto over 3 hours while stirring. The obtained mixture was stirred for 5 hours at the same temperature followed by cooling to room temperature. To the obtained reaction mixture, 16 g of 10% by weight hydrochloric acid was added dropwise over 30 minutes at 25 to 30° C. followed by stirring for 30 minutes at the same temperature. Further, 45% by weight aqueous sodium hydroxide solution was added thereto to adjust to pH 8. The obtained solution was concentrated. To the concentrated liquid, 50 g of ethyl acetate was added and the extraction procedure was repeated twice. The obtained organic layers were mixed and dried over anhydrous magnesium sulfate. After removing magnesium sulfate by filtration, the obtained filtrate was concentrated until the all amounts thereof were reduced by 10 g. To the concentrated liquid, 30 g of toluene was added and then the crystals were precipitated. The precipitated crystals were filtered and dried to obtain 3.82 g of white crystals of 2,3,5,6-tetrafluorobenzenedimethanol. The crystals were analyzed by liquid chromatography area percentage method to find out that the content thereof was 95.5%. Yield: 87%.

Example 14

<Step (B)>

Into a 200 mL flask equipped with a reflux condenser, 830 mg of sodium borohydride, 10 g of tetrahydrofuran and 2.66 g of dimethyl 2,3,5,6-tetrafluoroterephthalate were charged. The obtained mixture was adjusted to 65° C. and then, a solution obtained by mixing 395 mg of water with 10 g of tetrahydrofuran was added dropwise thereto over 3 hours while stirring. The obtained mixture was stirred for 2 hours at the same temperature followed by cooling to room temperature. To the obtained reaction mixture, 20 g of 10% by weight hydrochloric acid was added dropwise over 30 minutes at 25 to 30° C. followed by stirring for 1 hour at the same temperature. The obtained mixture was extracted twice with 30 g of ethyl acetate. The obtained organic layers were mixed and washed with 10 g of water to obtain a solution containing 2,3,5,6-tetrafluorobenzenedimethanol. The solution was analyzed by liquid chromatography internal standard method to find out that the yield thereof was 86%.

Example 15

<Step (B)>

Into a 200 mL flask equipped with a reflux condenser, 2.58 g of sodium borohydride and 25 g of dimethoxyethane were charged. The obtained mixture was adjusted to 50° C. and then, a solution obtained by mixing 6.10 g of 2,3,5,6-tetrafluoroterephthalic acid with 20 g of dimethoxyethane was added dropwise thereto over 1 hour while stirring. The obtained mixture was stirred for 7 hours at 60° C. To the obtained reaction mixture, 20 g of toluene was added followed by cooling to 50° C. Eight point five grams of 35% by weight hydrochloric acid was added dropwise thereto over 1 hour to stir at 60° C. for 6 hours. To the obtained mixture, 30 g of water was added followed by separating to an organic layer and an aqueous layer. The aqueous layer was extracted twice with 30 g of ethyl acetate. The obtained organic layers were mixed and washed with 10 g of a saturated aqueous potassium carbonate solution and then with 10 g of water. The organic layer was concentrated and the obtained solids were recrystallized with toluene and hexane to obtain white powder crystals of 2,3,5,6-tetrafluorobenzenedimethanol. The crystals were analyzed by liquid chromatography absolute calibration curve method to find out that the purity thereof was 95.1%. Yield: 95%.

Example 16

<Step (B)>

Into a 100 mL flask equipped with a reflux condenser, 1.03 g of sodium borohydride and 9.0 g of sulfolane were charged at room temperature, and the obtained mixture was heated to 50° C. A solution prepared by mixing 3.27 g of 2,3,5,6-tetrafluoroterephthaloyl difluoride, 21.0 g of sulfolane and 4.3 g of toluene was added dropwise thereto over 20 minutes. The obtained mixture was stirred for 1 hour at the same temperature followed by cooling to room temperature. To the obtained reaction mixture, 1.0 g of acetone, 86.7 g of toluene and 210 g of water were added followed by stirring and leaving at rest. The upper organic layer was obtained and 50 g of 50% by weight sulfuric acid was added thereto, and mixed with the lower aqueous layer to obtain an aqueous layer containing 2,3,5,6-tetrafluorobenzenedimethanol. The aqueous layer was analyzed by liquid chromatography internal standard method to find out that the yield thereof was 86%.

Example 17

<Step (C)>

Into a 50 mL flask equipped with a reflux condenser, 500 mg of 2,3,5,6-tetrafluorobenzenedimethanol, 3 g of toluene and 2.5 g of 36% by weight hydrochloric acid were charged followed by heating to 90° C. to conduct the reaction for 5 hours. The reaction mixture was cooled to room temperature and then, left at rest to separate to an organic layer and an aqueous layer. The obtained aqueous layer was extracted twice with 5 g of toluene. The obtained organic layers were mixed and concentrated to 545 mg of white crystals of 4-chloromethyl-2,3,5,6-tetrafluorobenzyl alcohol. The crystals were analyzed by gas chromatography area percentage method to find out that the purity thereof was 99.0%. Yield: 99%.

In the crystals, 0.8% of 1,4-bis(chloromethyl)-2,3,5,6-tetrafluorobenzene was contained.

Example 18

<Step (C)>

Into a 100 mL flask equipped with a reflux condenser, 6.6 g of 2,3,5,6-tetrafluorobenzenedimethanol (purity: 90%), which was obtained in Examples 10 and 11, 40 g of toluene and 33 g of 36% by weight hydrochloric acid were charged followed by heating to 90° C. to conduct the reaction for 5 hours. The reaction mixture was cooled to room temperature and then, left at rest to separate to an organic layer and an aqueous layer. The obtained aqueous layer was extracted twice with 10 g of toluene. The obtained organic layers were mixed and concentrated to 6.2 g of white crystals of 4-chloromethyl-2,3,5,6-tetrafluorobenzyl alcohol. The crystals were analyzed by gas chromatography area percentage method to find out that the purity thereof was 98.0%. Yield: 93%.

In the crystals, 0.5% of 1,4-bis(chloromethyl)-2,3,5,6-tetrafluorobenzene was contained.

The aqueous layer obtained after extracting with toluene was neutralized with 5% by weight aqueous sodium hydroxide solution followed by extracting with toluene. The obtained organic layer was concentrated to recover 0.1 g of 2,3,5,6-tetrafluorobenzenedimethanol.

Comparative Example 1

Into a 100 mL flask equipped with a reflux condenser, 13.3 g of 2,3,5,6-tetrafluorobenzenedimethanol (purity: 90%), 70 g of toluene and 16.4 g of 48% by weight hydrobromic acid were charged followed by heating to 90° C. to conduct the reaction for 4 hours. The reaction mixture was cooled to room temperature and then, left at rest to separate to an organic layer and an aqueous layer. The obtained aqueous layer was extracted twice with 10 g of toluene. The obtained organic layers were mixed and concentrated to 14.9 g of white crystals of 4-bromomethyl-2,3,5,6-tetrafluorobenzyl alcohol. The crystals were analyzed by gas chromatography area percentage method to find out that the purity thereof was 90.0%. Yield: 86%.

In the crystals, 8.0% of 1,4-bis(bromomethyl)-2,3,5,6-tetrafluorobenzene was contained.

Example 19

<Step (C)>

Into a 120 mL autoclave, 7.0 g of 2,3,5,6-tetrafluorobenzenedimethanol (purity: 99.1%), 42 g of toluene and 34.7 g of 35% by weight hydrochloric acid were charged followed by sealing and then heating to 90° C. to conduct the reaction for 5 hours. The maximum value of the pressure during the reaction was 0.12 MPa (gauge pressure). The reaction mixture was cooled to room temperature and then, left at rest to separate to an organic layer and an aqueous layer. The obtained aqueous layer was extracted with 25 g of toluene. The obtained organic layers were mixed and concentrated to obtain 7.4 g of white crystals of 4-chloromethyl-2,3,5,6-tetrafluorobenzyl alcohol. The crystals were analyzed by gas chromatography area percentage method to find out that the purity thereof was 96.6%. Yield: 94%.

In the crystals, 2.9% of 1,4-bis(chloromethyl)-2,3,5,6-tetrafluorobenzene was contained.

Example 20

<Step (D)>

Into a 100 mL flask equipped with a reflux condenser, 1.2 g of 5% by weight palladium/carbon (containing water of 50% by weight), 6.1 g of 4-chloromethyl-2,3,5,6-tetrafluorobenzyl alcohol obtained in Example 18, and 30 g of n-butanol were charged. The substitution of the gas phase part inside the flask with nitrogen was conducted followed by substituting with hydrogen, and then a 1 L-volume rubber balloon filled with hydrogen was equipped to the flask. The mixture was heated to 100° C. to conduct the reaction for 16 hours at the same temperature while stirring. The reaction mixture was cooled to room temperature. The catalyst was removed by filtration, and the catalyst was washed with 10 g of ethyl acetate. The filtrate and the wash liquid were mixed to concentrate to obtain white crystals of 4.7 g of white crystals of 4-methyl-2,3,5,6-tetrafluorobenzyl alcohol. The crystals were analyzed by gas chromatography area percentage method to find out that the purity thereof was 98%. Yield: 90%.

Example 21

<Step (D)>

Into a 120 mL autoclave, 0.16 g of 5% by weight palladium/carbon (containing water of 54% by weight), 8.6 g of 4-chloromethyl-2,3,5,6-tetrafluorobenzyl alcohol (purity: 92.7%), 0.6 g of water, 1.8 g of magnesium oxide and 52 g of methanol were charged. The substitution inside the container with nitrogen was conducted followed by pressurized to 0.35 MPa (gauge pressure) with hydrogen. The mixture was heated to 50° C. to conduct the reaction for 6 hours at the same temperature while maintaining the pressure of 0.35 MPa. The reaction mixture was cooled to room temperature. The catalyst was removed by filtration, and the catalyst was washed with 43 g of toluene. The filtrate and the wash liquid were mixed to concentrate to obtain white crystals of 6.9 g of white crystals of 4-methyl-2,3,5,6-tetrafluorobenzyl alcohol. The crystals were analyzed by gas chromatography area percentage method to find out that the purity thereof was 92.3%. Yield: 94%.

INDUSTRIAL APPLICABILITY

According to the present invention, 4-methyl-2,3,5,6-tetrafluorobenzyl alcohol can be produced advantageously.

The invention claimed is:

1. A process for producing 4-methyl-2,3,5,6 tetrafluorobenzyl alcohol comprising the following steps (A) to (D):
    Step (A): a step for fluorinating 2,3,5,6-tetrachloroterephthaloyl dichloride using potassium fluoride, wherein the potassium fluoride is a potassium fluoride composition obtained by mixing a mixture containing potassium fluoride and 5 to 50 parts by weight of methanol per 1 part by weight of potassium fluoride with an aprotic organic solvent having a boiling point higher than that of methanol, followed by removing methanol by distillation from the obtained mixture,
    Step (B): a step for reducing the product obtained in step (A),
    Step (C): a step for chlorinating the product obtained in step (B), and
    Step (D): a step for hydrogenating the product obtained in step (C).

2. The process according to claim 1, wherein the fluorination is conducted in the presence of dimethyl sulfone in step (A).

3. The process according to claim 1, wherein the product obtained in step (A) is tetrafluoroterephthaloyl difluoride.

4. The process according to claim 1, wherein step (A) further contains an operation for mixing the reaction mixture obtained by fluorination with water.

5. The process according to claim 4, wherein the product obtained in step (A) is 2,3,5,6-tetrafluoroterephthalic acid.

6. The process according to claim 1, wherein step (A) further contains an operation for mixing the reaction mixture obtained by fluorination with a C1-C6 alcohol compound.

7. The process according to claim 6, wherein the product obtained in step (A) is 2,3,5,6-tetrafluoroterephthalic acid diester.

8. The process according to claim 1, wherein the reduction is conducted using at least one selected from the group consisting of a borohydride compound, an aluminum hydride compound and a silicon hydride compound in step (B).

9. The process according to claim 1, wherein the reduction is conducted using an alkali metal borohydride in step (B).

10. The process according to claim 9, wherein the alkali metal borohydride is sodium borohydride.

11. The process according to claim 9, wherein the reduction is conducted in the presence of at least one selected from the group consisting of an acid, water and a C1-C10 alcohol compound in step (B).

12. The process according to claim 1, wherein the product obtained in step (B) is 2,3,5,6-tetrafluoro-1,4-benzenedimethanol.

13. The process according to claim 1, wherein the chlorination is conducted using hydrogen chloride in step (C).

14. The process according to claim 13, wherein the chlorination is conducted in a two-layer system in step (C).

15. The process according to claim 1, wherein the product obtained in step (C) is 4-chloromethyl-2,3,5,6-tetrafluorobenzyl alcohol.

16. The process according to claim 1, wherein the hydrogenation is conducted using hydrogen in the presence of a metal catalyst in step (D).

17. The process according to claim 16, wherein the hydrogenation is conducted in the presence of a base in step (D).

* * * * *

UNITED STATES PATENT AND TRADEMARK OFFICE
CERTIFICATE OF CORRECTION

PATENT NO.        : 8,039,680 B2                        Page 1 of 1
APPLICATION NO.   : 12/525913
DATED             : October 18, 2011
INVENTOR(S)       : Koji Hagiya It is certified that error appears in the above-identified patent and that said Letters Patent is hereby corrected as shown below:

Title Page, Section (22):

The PCT filing date should be -- Feb. 14, 2008 --.

Signed and Sealed this
Twenty-seventh Day of March, 2012

David J. Kappos
*Director of the United States Patent and Trademark Office*